US008204294B2

(12) United States Patent
Alloo et al.

(10) Patent No.: US 8,204,294 B2
(45) Date of Patent: Jun. 19, 2012

(54) SYSTEMS AND METHODS FOR DETECTING DEFECTS IN COATINGS UTILIZING COLOR-BASED THERMAL MISMATCH

(75) Inventors: Richard Alloo, Lexington, KY (US); Kozo Saito, Lexington, KY (US); Belal Gharaibeh, Lexington, KY (US); Keng Chuah, Lexington, KY (US); Nelson Akafuah, Lexington, KY (US); Ahmad Salaimeh, Lexington, KY (US)

(73) Assignees: Toyota Motor Engineering & Manufacturing North America, Inc., Erlanger, KY (US); University of Kentucky Research Foundation, Lexington, KY (US)

( * ) Notice: Subject to any disclaimer, the term of this patent is extended or adjusted under 35 U.S.C. 154(b) by 415 days.

(21) Appl. No.: 12/626,381

(22) Filed: Nov. 25, 2009

(65) Prior Publication Data

US 2011/0123093 A1    May 26, 2011

(51) Int. Cl.
*G06K 9/00*    (2006.01)
(52) U.S. Cl. ............... 382/141; 382/152; 382/164
(58) Field of Classification Search ............ 382/141, 382/152, 164; 356/402
See application file for complete search history.

(56) References Cited

U.S. PATENT DOCUMENTS

| 3,020,745 | A | 2/1962 | Sielicki |
| 4,109,508 | A | 8/1978 | Fukuyama |
| 4,480,928 | A | 11/1984 | Halsor et al. |
| 4,633,594 | A | 1/1987 | Bovone |
| 4,634,291 | A | 1/1987 | Bantel et al. |
| 4,818,118 | A | 4/1989 | Bantel et al. |
| 4,905,842 | A | 3/1990 | Habele et al. |
| 4,996,426 | A | 2/1991 | Cielo et al. |
| 5,032,727 | A | 7/1991 | Cox, Jr. et al. |
| 5,075,552 | A | 12/1991 | McClelland et al. |
| 5,091,647 | A | 2/1992 | Carduner et al. |
| 5,111,048 | A | 5/1992 | Devitt et al. |
| 5,294,198 | A | 3/1994 | Schlagheck |

(Continued)

FOREIGN PATENT DOCUMENTS

JP          62-198707          9/1987

(Continued)

OTHER PUBLICATIONS

NP. Avdelidis, B.C. Hawtin and D.P. Almond "Transient Thermography in the Assessment of Defects of Aircrafts Composites" NDT and E International, vol. 36 Issue 6, pp. 433-439 Sep. 2003.

(Continued)

*Primary Examiner* — Roy M Punnoose
(74) *Attorney, Agent, or Firm* — Dinsmore & Shohl LLP

(57) ABSTRACT

A method of analyzing a thermal image of a coated substrate to determine the presence of defects includes determining a defect temperature range based on a color of the coated substrate and the maximum temperature of the coated substrate in the thermal image. Thereafter, the thermal image is processed by determining a signal value of a pixel of interest based on a temperature of the pixel of interest, temperatures of pixels in a kernel of pixels surrounding the pixel of interest, and the color of the coated substrate. The signal value of the pixel of interest is then compared to the lower temperature threshold of the defect temperature range, wherein the pixel of interest is a defect location when the signal value of the pixel of interest is greater than or equal to the lower temperature threshold.

20 Claims, 10 Drawing Sheets

U.S. PATENT DOCUMENTS

| | | | |
|---|---|---|---|
| 5,358,333 | A | 10/1994 | Schmidt et al. |
| 5,376,793 | A | 12/1994 | Lesniak |
| 5,402,364 | A | 3/1995 | Kitoh et al. |
| 5,631,465 | A | 5/1997 | Shepard |
| 5,711,603 | A | 1/1998 | Ringermacher et al. |
| 5,808,303 | A | 9/1998 | Schlagheck et al. |
| 6,000,844 | A | 12/1999 | Cramer et al. |
| 6,013,915 | A | 1/2000 | Watkins |
| 6,271,878 | B1 | 8/2001 | Sera |
| 6,339,337 | B1 | 1/2002 | Matsuda et al. |
| 6,346,704 | B2 | 2/2002 | Kenway |
| 6,399,949 | B1 | 6/2002 | Roney, Jr. et al. |
| 6,400,128 | B2 | 6/2002 | Guidotti et al. |
| 6,408,917 | B1 | 6/2002 | Bett et al. |
| 6,452,180 | B1 | 9/2002 | Nistler et al. |
| 6,461,035 | B2 | 10/2002 | Meinlschmidt et al. |
| 6,491,426 | B1 | 12/2002 | Schonath et al. |
| 6,495,833 | B1 | 12/2002 | Alfano et al. |
| 6,515,284 | B1 | 2/2003 | Walle et al. |
| 6,517,238 | B2 | 2/2003 | Sun et al. |
| 6,751,342 | B2 | 6/2004 | Shepard |
| 7,129,492 | B2 | 10/2006 | Saito et al. |
| 7,220,966 | B2 * | 5/2007 | Saito et al. ............... 250/341.6 |
| 2001/0042834 | A1 | 11/2001 | Kenway |
| 2002/0018510 | A1 | 2/2002 | Murphy et al. |
| 2002/0044679 | A1 | 4/2002 | Shepard |
| 2002/0050566 | A1 | 5/2002 | Nilsson et al. |
| 2005/0186327 | A1 * | 8/2005 | Saito et al. ..................... 427/8 |

FOREIGN PATENT DOCUMENTS

| | | |
|---|---|---|
| JP | 63-085438 | 4/1988 |
| JP | 1156650 | 6/1989 |
| JP | 02-022547 A | 1/1990 |
| JP | 6341965 | 12/1994 |
| JP | 3079920 | 6/1996 |
| JP | 8145922 | 6/1996 |
| JP | 10-096705 | 4/1998 |
| WO | WO 2008/071204 | 6/2008 |

OTHER PUBLICATIONS

E. Grinzato, V. Vavilov, T. Kauppinen. "Quantative Infrared Thermography in Buildings" Energy and Buildings 29, pp. 1-9 1998.

Ch. Maierhofer, A. Brink, M. Rollig and H. Wiggenhauser "Detection of Shallow Voids in Concrete Structures with Impulse Thermography and Radar" NDT and E International, vol. 36 Issue 4, pp. 257-263, Jun. 2003.

P.J. Fito, M.D. Ortola, R.D. De los Reyes, P. Fito and E. De los Reyes "Control of Citrus Surface Drying by Image Analysis of Infrared Thermography" Journal of Food Engineering, vol. 61 Issue 3, pp. 287-290, Feb. 2004.

Balageas D., Deom A., Boscher D., "Characterization and Nondestructive Testing of Carbon-epoxy Composites by a Pulsed Photothermal Method." Materials Evaluation, vol. 45, 1987.

D.P. Almond and S.K. Lau "Defect Sizing by Transient Thermography. I: An Analytical Treatment" J Phys D: Appl Phys vol. 27 pp. 1063-1069, 1994.

M.B. Saintey and D.P. Almond "Defect Sizing by Transient Thermography. II: A Numerical Treatment" J Phys D: Appl Phys vol. 28, pp. 2539-2546, 1995.

N.K. Del Grande and P.F. Dubrin, "Mapping Hidden Aircraft Defect with Dual Band Infrared Computed Tomography" Proc. Of SPIE V. 2455 Jun. 6-8, pp. 82-93 1992.

N.P. Avdelidis and D.P. Almond "Transient Thermography as a Through Skin Imaging Technique for Aircraft assembly: Modeling and Experimental results" Infrared Physics and Technology, vol. 45 Issue 2, pp. 103-114, Mar. 2004.

H.G. Walther "Surface Roughness Influence on Photothermal Radiometry" Applied Surface Science, vol. 193 Issue 1-4, pp. 156-166, Jun. 2002.

S. Shepard, B.A. Rubadeux and T. Ahmed "Automated Thermographic Defect Recognition and Measurement." Nondestructive Characterization of Materials IX, American Institute of Physics 1999.

Takahide Sakagami, Shiro Kubo "Applications of Pulse Heating Thermography and Lock-in Thermography to Quantative Nondestructive Evaluations" Infrared Physics and Technology vol. 43 pp. 211-218 2002.

Gary Shubinsky "Visual & Infrared Imaging for Bridge Inspection" Northwestern University BIRL Basic Industrial Research Laboratory, Jun. 1994.

L.D. Favro, Xiaoyan Han, and R.L. Thomas "Thermal-Wave Imaging for NDE of Composites" pp. 1077-1081, Proceedings of the American Society for composites Twelfth Technical Conference: Oct. 6-8, 1998 Dearborn Inn, Dearborn Michigan.

D.J. Titman Applications of Thermography in Non-destructive Testing of Structures: NDT and E International vol. 34 pp. 149-154, 2001.

A. Wyckhuyse, X. Maldague, "Study of Wood Inspection by Infrared Thermography, Part I: Wood Pole Inspection by Infrared Thermography" Research in Nondestructive Evaluation, 13. Issue 1, pp. 1-12, Mar. 2001.

A. Wyckhuyse, X. Maldague, "Study of Wood Inspection by Infrared Thermography, Part II: Wood Pole Inspection by Infrared Thermography" Research in Nondestructive Evaluation, 13. Issue 1, Mar. 2001.

V. Vavilov, V. Demin, "Infrared Thermographic Inspection of Operating Smokestacks" Infrared Physics and Technology 43. pp. 229-232, 2002.

S. Shepard, R. Ducar. "Quantative Infrared Defect Detection in composite Aerospace Structures." 45th International SAMPE Symposium 2000.

T. Sakagami, et al. "Development of a pulse heating thermographic NDT technique for detection of latent blister in corrosion protective coating on oil storage tank", Thermosense XXIII Proc, 4360, Orlando, Florida 2001.

P.G. Bison, S. Marinetti, E. Grinzato, V. Vavilov, F. Cernuschi, Dr. Robba "Inspecting thermal barrier coatings by IR thermography" Thermosense XXV, K. Elliot Cramer, Xavier P. Maldague, Editors, Proceedings of SPIE 5073 (2003).

Oslander R, Spicer JWM, Murphy JC, "Analysis methods for full field time resolved radiometry" in Burleigh DD, Spicer JWM, eds. Thermosense XVIII, SPIE Proc. 2766:218-227, 1996.

Turler D. "Predicting the geometry and location of defects in adhesive and spot welded lap joints using steady state thermographic techniques" Thermosense XXI, 3700 Orlando-Florida, pp. 54-62, Apr. 6-8, 1999.

H. Aglan, S. Shroff, Z. Abdo, T. Ahmed, L. Wang, L.D. Favro and R.L. Thomas. "Cumulative fatigue disbond of adhesive joints and its detection using thermal wave imaging" Review of progress in quantitative non-destructive evaluation. 14, p. 431-438, 1995.

D.A. Tossell "Numerical analysis of heat input effects in thermography" Journal of nondestructive testing 6 No. 2 1987.

X. Maldague, F. Galmiche, A. Ziadi "Advances in pulsed phased thermography". Infrared Physics and Technology 43, pp. 175-181, 2002.

S. Shepard, et al. "Reconstruction and enhancement of active thermographic image sequences" Optical Engineering 42 (5) pp. 1337-1342, May 2003.

X. Maldague, J. Cote, D. Poussart, V. Valvilov "Thermal Tomography for NDT of industrial materials" Canadian Society of Nondestructive Testing Journal pp. 22-32, May-Jun. 1992.

Vavilov V. "Dynamic Thermal Tomography: Perspective Field of Thermal NDT" in Semanovich SA, ed. Thermosense XI, SPIE Proceedings, 1313. pp. 178-182, 1990.

L.D. Favro, et al. "Thermal Wave Imaging of Aircraft Structures" Review of Progress in Quantitative Non-destructive Evaluation, 14, pp. 461-466, 1995.

V. Vavilov, X. Maldague "Dynamic Thermal Tomography: New Promise in the IR Thermography of Solids" SPIE vol. 1682, Thermosense XIV, pp. 194-206, 1992.

X. Maldague "Theory and Practice of Infrared Technolgy for Nondestructive Testing" Wiley Interscience Publication, Chapters 1,6,11. 2001.

Feeler, Robert A., "Infrared Thermography Offers New Possibilities for Nondestructive Testing," Flight Safety Foundation, Aviation Mechanics Bulletin, May-Jun. 1995.

"Heat Conduction in Solids with Buried Discontinuities," Nondestructive Testing Handbook, Infrared and Thermal Testing, Third Edition, vol. 3, p. 62, Mar. 2001.

Favro, L.D., Xiaoyan Han, P.K. Kuo and R.L. Thomas, "Measuring Defect Depths by Thermal-Wave Imaging," Thermosense XVIII: An International Conference on Thermal Sensing and Imaging Diagnostic Applications, vol. 2766, pp. 236-239, Mar. 1996.

* cited by examiner

SYSTEMS AND METHODS FOR DETECTING DEFECTS IN COATINGS UTILIZING COLOR-BASED THERMAL MISMATCH

TECHNICAL FIELD

The present specification generally relates to systems and methods for detecting defects in coatings and, more specifically, to systems and methods for detecting defects in coated substrates utilizing infrared thermography in conjunction with color-based thermal mismatch.

BACKGROUND

The finish of a product or object, such as the visible surface of a painted object, plays an important role in a consumer's perception of the quality of the object. Accordingly, for high quality automobiles and other vehicles and/or articles of manufacture, the inspection of coatings, such as paint coatings, for defects is an important part of quality control. For example, the body panels of an automobile may receive at least four coatings including a protective coat, an adhesion aid coat, a paint coat and a clear coat. Defects occurring in any one of the coatings applied to a properly prepared substrate or surface may diminish a consumer's perception of the automobile. Such defects may include, but are not limited to, dust, hair, metallic particles, coating over spray, incomplete spray, stripping and flake penetration.

In order to identify defects in a coating each coating may be evaluated after application. Previously, evaluation of the quality of a coating was often based on human inspection, which can be a tedious and subjective process which requires meaningful skill and training. Other, automated inspection procedures have been developed which use charge-coupled device (CCD) optical sensors that sense imperfections through light reflected from the coated surface. However, this technique is not particularly effective for complex, curved and/or hidden geometries (i.e. automobile body panels) because of its sensitivity and dependence on reflection and scattering angles.

Other inspection techniques have been developed which use infrared cameras to inspect certain products (i.e. semiconductor chips) for surface anomalies or defects. However, such inspection techniques are based solely on the spatial analysis of pixel values with that of known (standard) values without any account for the temporal behavior of the pixel values (e.g., change of temperature over time). Further, while other techniques have been utilized to measure the change of temperature over time, such techniques do not compare the measured change of temperature of pixels to that of surrounding pixels, and therefore fail to efficiently and effectively detect subsurface anomalies. Moreover, many inspection procedures require comparison to a known non-defective area within a thermal profile for thermal deviation determinations while others require continuous acquisition of a sequence of data files. Such procedures can also require operator intervention, significant time requirements, and/or computational complexities not suited for realtime applications.

Accordingly, a need exists for alternative methods and systems for inspecting a substrate for defects which may be present in a coating applied to the substrate.

SUMMARY

In one embodiment, a method of analyzing a thermal image of a coated substrate to determine the presence of defects includes determining a color of the coated substrate and determining a maximum temperature of the coated substrate. A defect temperature range is determined based on the color of the coated substrate and the maximum temperature of the coated substrate. A pixel of interest is also identified. Thereafter, the thermal image is processed by determining a signal value of the pixel of interest based on a temperature of the pixel of interest, temperatures of pixels in a kernel of pixels surrounding the pixel of interest, and the color of the coated substrate. The signal value of the pixel of interest is then compared to the lower temperature threshold of the defect temperature range, wherein the pixel of interest is a defect location when the signal value of the pixel of interest is greater than or equal to the lower temperature threshold.

In another embodiment, a method for detecting defects in a coated substrate includes determining a color of the coated substrate. The temperature of the coated substrate is manipulated and a thermal image of the coated substrate is acquired. The maximum temperature of the coated substrate is determined from the thermal image. A defect temperature range is determined based on a color of the coated substrate and the maximum temperature of the coated substrate in the thermal image and a pixel of interest is identified. Thereafter, the thermal image is processed by determining a signal value of a pixel of interest based on a temperature of the pixel of interest, temperatures of pixels in a kernel of pixels surrounding the pixel of interest, and the color of the coated substrate. The signal value of the pixel of interest is then compared to the lower temperature threshold of the defect temperature range, wherein the pixel of interest is a defect location when the signal value of the pixel of interest is greater than or equal to the lower temperature threshold.

In yet another embodiment, a defect detection system for detecting a defect in a coated substrate includes a thermal detector electrically coupled to a controller and at least one temperature manipulation device electrically coupled to the controller. The controller is programmed to: receive an input indicative of a color of the coated substrate; manipulate a temperature of the coated substrate with the temperature manipulation device; acquire a thermal image of the coated substrate with the thermal detector; determine a maximum temperature of the coated substrate from the thermal image; determine a defect temperature range based on the color of the coated substrate and the maximum temperature of the coated substrate; identify a pixel of interest; and process the thermal image by determining a signal value of a pixel of interest based on a temperature of the pixel of interest, temperatures of pixels in a kernel of pixels surrounding the pixel of interest, and the color of the coated substrate and comparing the signal value of the pixel of interest to a lower temperature threshold of the defect temperature range, wherein the pixel of interest is a defect location when the signal value of the pixel of interest is greater than or equal to the lower temperature threshold.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
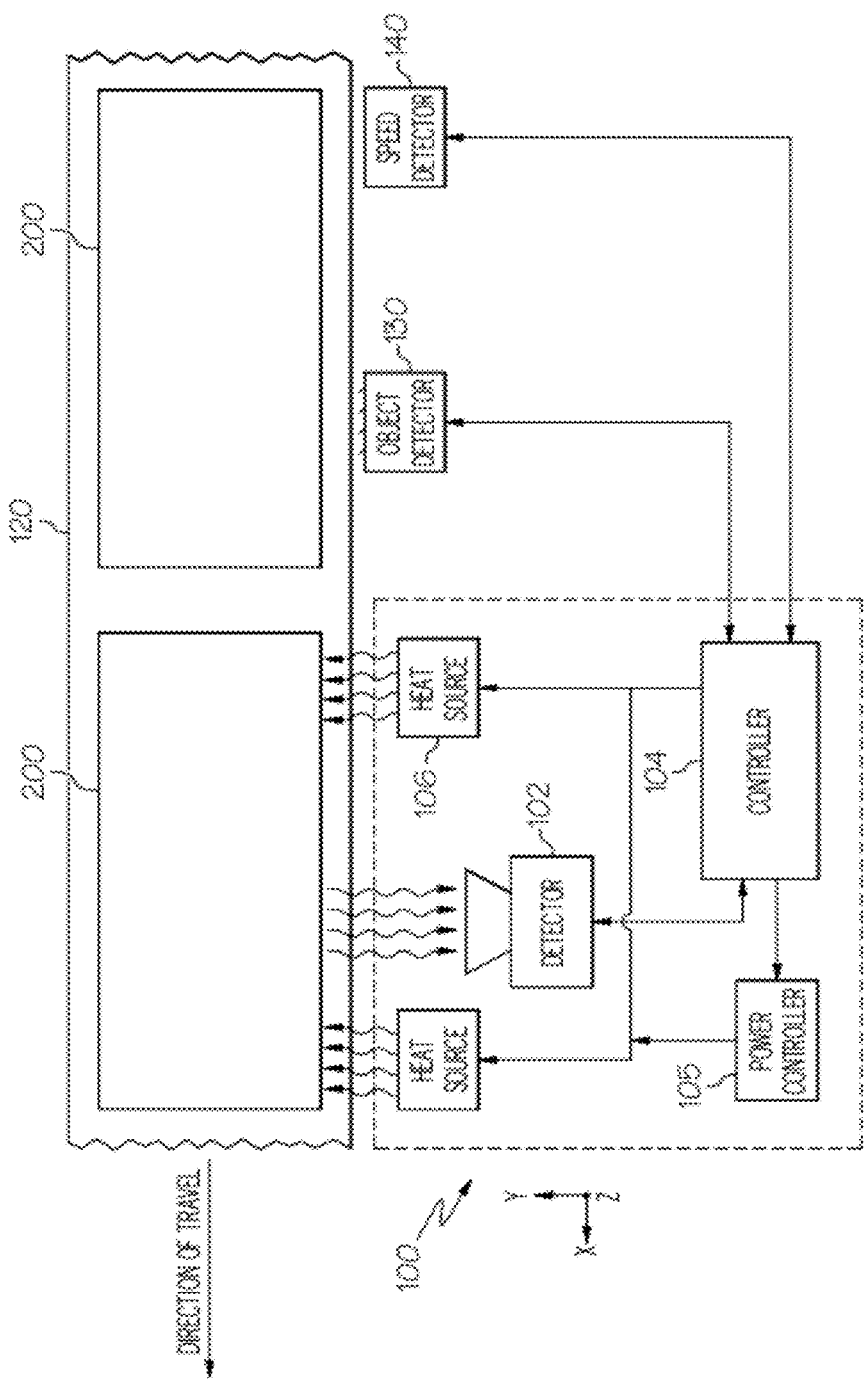
FIG. 1 depicts a defect detection system for detecting a defect in a coating utilizing color-based thermal mismatch according to one or more embodiments shown and described herein.

FIG. 1 generally depicts one embodiment of a defect detection system for inspecting a coated substrate to identify defects which may be present in the coating. The defect detection system generally comprises a controller, an object detector coupled to the controller for determining a color of the coated substrate, a temperature manipulation device coupled to the controller for manipulating the temperature of the coating applied to the substrate, and a thermal detector for collecting a thermal image of the coating on the substrate after the temperature of the coating has been manipulated. The defect detection system, the principles of operation of the defect detection system, and methods of using the defect detection system will be described in more detail herein.

The defect detection system 100 depicted in FIG. 1 and described herein operates on the principle of thermal mismatch between the defect and the coating layer(s) in which the defect is present. In particular, when the temperature of a surface and/or coating(s) containing a defect is manipulated (i.e., increased or decreased), the thermal effusivity and thermal diffusivity of the defect and the coating(s) in which the defect is contained may be different and, as such, the defect and the coating may have different changes in temperature in response to the thermal manipulation. Using this principle, a thermal detector, such as an infrared camera or a similar detector, may be used to monitor the changes in the temperature of both the defect and the coating and, utilizing the aforementioned principle, distinguish the defect from the coating.

More particularly, the thermal diffusivity of a material is a measure of the rate at which thermal energy (i.e., heat) may diffuse through a material. Generally, materials that have high thermal conductivity also have high thermal diffusivity and respond more quickly to changes in temperature than do materials with low thermal conductivity. The thermal diffusivity a of a material may be expressed by the Parker Flash equation as follows:

$$\alpha = \frac{1.38 L^2}{\pi^2 t_{1/2}}, \quad (1)$$

where L is the thickness of the material and $t_{1/2}$ is the time it takes to raise the temperature of the material to 50% of its maximum for a given thermal input. Alternatively, the thermal diffusivity may also be expressed in terms of the thermal properties of the material such that:

$$\alpha = \frac{\kappa}{\rho c_p}, \quad (2)$$

where κ is the thermal conductivity of the material, ρ is the density of the material, and $c_p$ is the specific heat of the material. The product of ρ and $c_p$ may be written as $$\rho c_p = \frac{Q}{L \Delta T_{max}}, \quad (3)$$

where Q is an applied thermal energy per unit area, L is the thickness of the material and $\Delta T_{max}$ is the maximum change in temperature of the material due to the applied thermal energy.

The thermal effusivity of a material is a measure of the ability of a material to increase its temperature in response to a given thermal input. More specifically, the thermal effusivity e (also referred to as thermal inertia) of a material may be expressed as:

$$e = \sqrt{\kappa \rho c_p} \quad (4),$$

where κ is the thermal conductivity of the material, ρ is the density of the material, and $c_p$ is the specific heat of the material. Based on the foregoing, the thermal effusivity of a material may be described as a function of the thermal diffusivity such that:

$$e = \frac{\kappa}{\sqrt{\alpha}} = \kappa \frac{\pi}{L} \sqrt{\frac{t_{1/2}}{1.38}}. \quad (5)$$

The difference between the thermal effusivity of a defect $e_d$ and the thermal effusivity of a coating $e_c$ in which the defect resides results in a thermal mismatch and, as such, a different thermal wave may be reflected or emitted from the defect compared to the thermal wave reflected or emitted from the coating. More specifically, the thermal mismatch Γ between the thermal effusivity of the defect $e_d$ and the thermal effusivity of the coating $e_c$ may be expressed mathematically as:

$$\Gamma = \frac{e_d - e_c}{e_d + e_c} = \frac{\sqrt{\kappa_d \rho_d c_{pd}} - \sqrt{\kappa_c \rho_c c_{pc}}}{\sqrt{\kappa_d \rho_d c_{pd}} + \sqrt{\kappa_c \rho_c c_{pc}}}. \quad (6)$$

As described above, the thermal mismatch between two materials results in different thermal waves being reflected or emitted from the materials. For example, considering an epoxy resin ($e_c$=667 W·$s^{0.5}$/$m^2$k) having an air pocket (i.e., a defect with $e_d$=9.19 W·$s^{0.5}$/$m^2$k), the thermal mismatch between the epoxy resin and the air pocket may be expressed as:

$$\Gamma = \frac{e_d - e_c}{e_d + e_c} = \frac{9.19 - 667}{9.19 + 667} \cong -0.97. \quad (7)$$

Thus, the thermal mismatch between the epoxy resin and the air pocket may be about 97%. Accordingly, the interface between the air pocket and the epoxy resin only reflects or emits approximately 97% of the thermal energy reflected by the epoxy resin without an air pocket (e.g., an epoxy resin with a defect).

It has now been determined that different colors may have different thermal effusivities e and, as such, the thermal effusivity of the color of a coating and/or substrate can be taken into account when determining the thermal mismatch between a coating and a possible defect in the coating thereby improving the resolution of defects in the coating.

Figure 2:
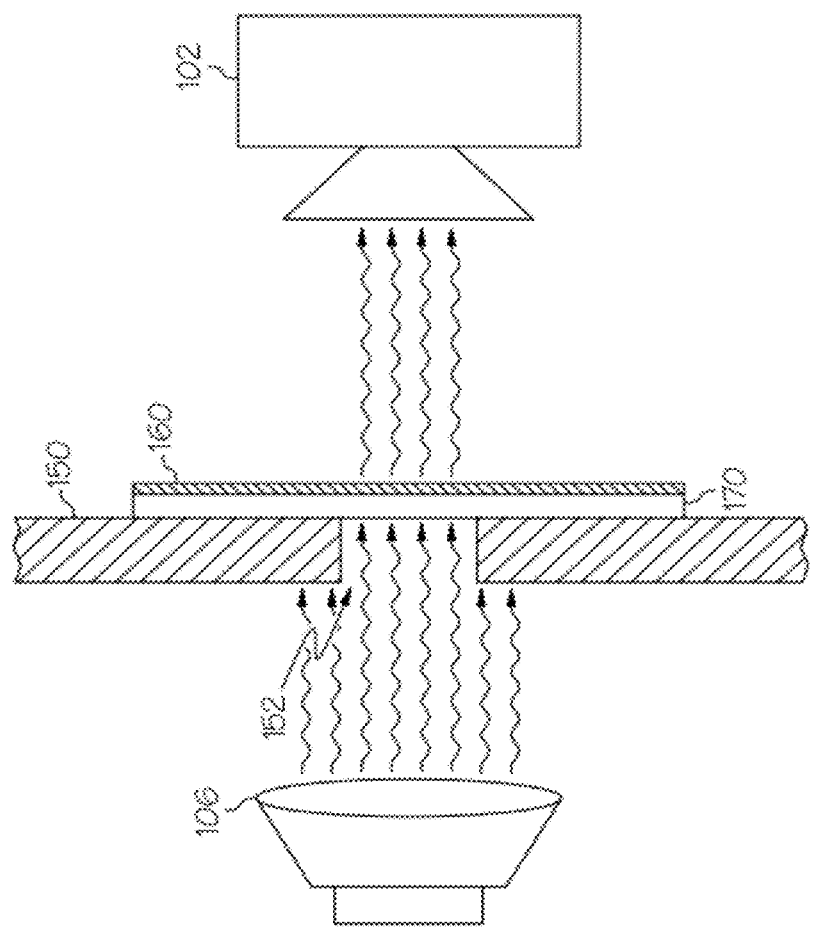
FIG. 2 depicts a test apparatus for determining the effect of color on the thermal effusivity of a coating applied to a substrate according to one or more embodiments shown and described herein.

Referring now to FIG. 2, an apparatus is shown for experimentally determining the effects of color on the thermal effusivity and thermal diffusivity of a coating. The experimental set up includes a temperature manipulation device 106, a heat shield 150, and a thermal detector 102. In the apparatus shown the temperature manipulation device 106 is an incandescent bulb capable of producing a light pulse of 500 µs with a power of 500 Watts. The thermal detector is an infrared camera. The heat shield 150 comprises a thermally insulating material which includes a window 152 which passes through the heat shield 150.

In order to determine the effect of color on thermal effusivity and thermal diffusivity, a substrate 170 having a colored coating 160 disposed thereon may be placed over the window. The temperature manipulation device 106 and thermal detector 102 are oriented on opposite sides of the window 152 such that the uncoated surface of the substrate 170 faces the temperature manipulation device 106 and the color coating 160 faces the thermal detector 102. The temperature manipulation device 106 is then activated and emits a pulse of light which heats the portion of the substrate 170 exposed in the window 152. The heat is propagated through the substrate 170 and into the color coating 160. The thermal detector 102 records the temperature of the colored coating 160 over time as the colored coating is heated and cools.

Table 1 contains the values for the thermal effusivity e of four different colored coatings which were calculated using Equation (4) in conjunction with experimental data (i.e., $t_{1/2}$) derived with the apparatus shown in FIG. 2. As shown in Table 1, each of the colored coatings had a similar thickness L. While the coatings have similar physical dimensions, each colored coating has a different thermal effusivity e.

Figure 3:
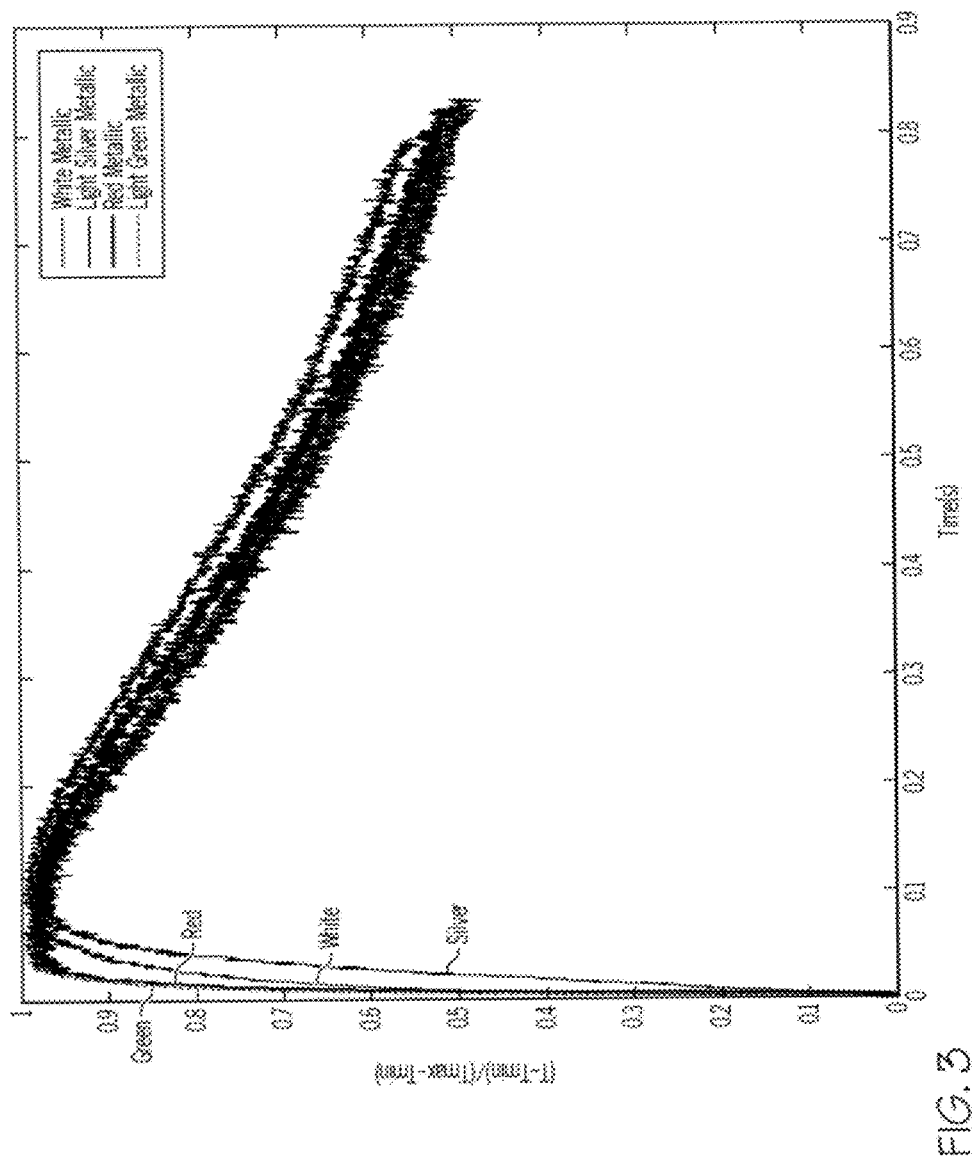
FIG. 3 depicts the temperature histories of four different colored coatings.
Figure 4:
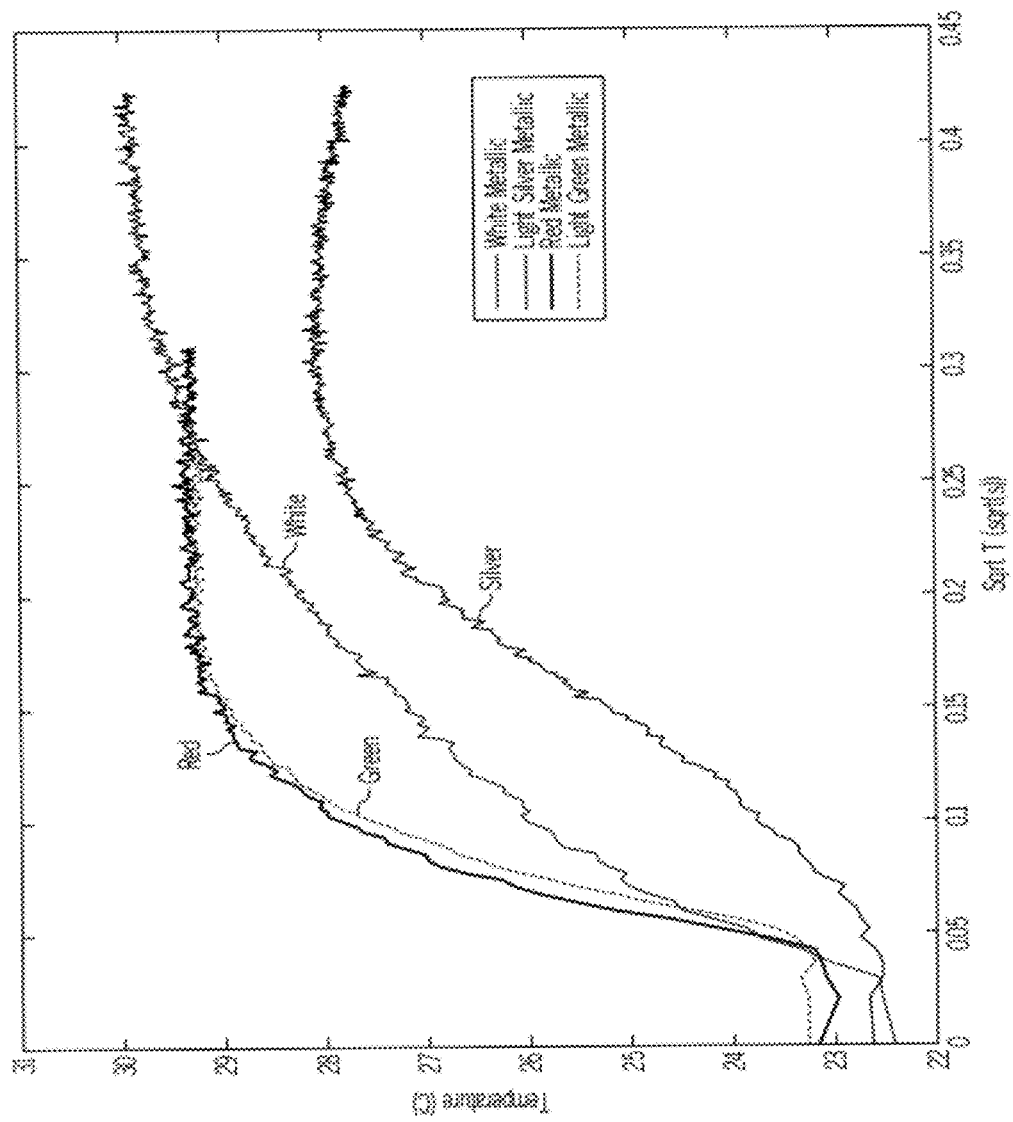
FIG. 4 depicts the temperature (y-axis) of four different colored coatings over the square root of time (x-axis) to illustrate the effect of the different thermal effusivities of each colored coating.

Referring now to FIGS. 3-4, FIG. 3 shows the temperature history for each of the four defect-free colored coatings of Table 1 as a result of being heated with the heat source. The y-axis is indicative of the normalized temperature ($(T-T_{mm})/(T_{max}-T_{min})$) while the x-axis is indicative of time in seconds. As shown in FIG. 3, each colored coating had a rapid increase in temperature to a maximum temperature followed by a gradual decrease in temperature after being heated by the heat source.

To better illustrate the effect of thermal effusivity on the temperature of the material, FIG. 4 shows the temperature of each of the four defect-free coatings of Table 1 on the y-axis while the x-axis depicts the square root of time. As shown in FIG. 4, each color has a different thermal response which is believed to be due to the different thermal effusivities of each of the colored coatings. For example, the red and the green colored coatings exhibit similar thermal behavior upon being heated, as illustrated in FIG. 4. However, the white and silver colored coatings have thermal effusivity values different from those of the red and green colored coatings and thus exhibit different thermal behavior upon being heated.

Figure 5:
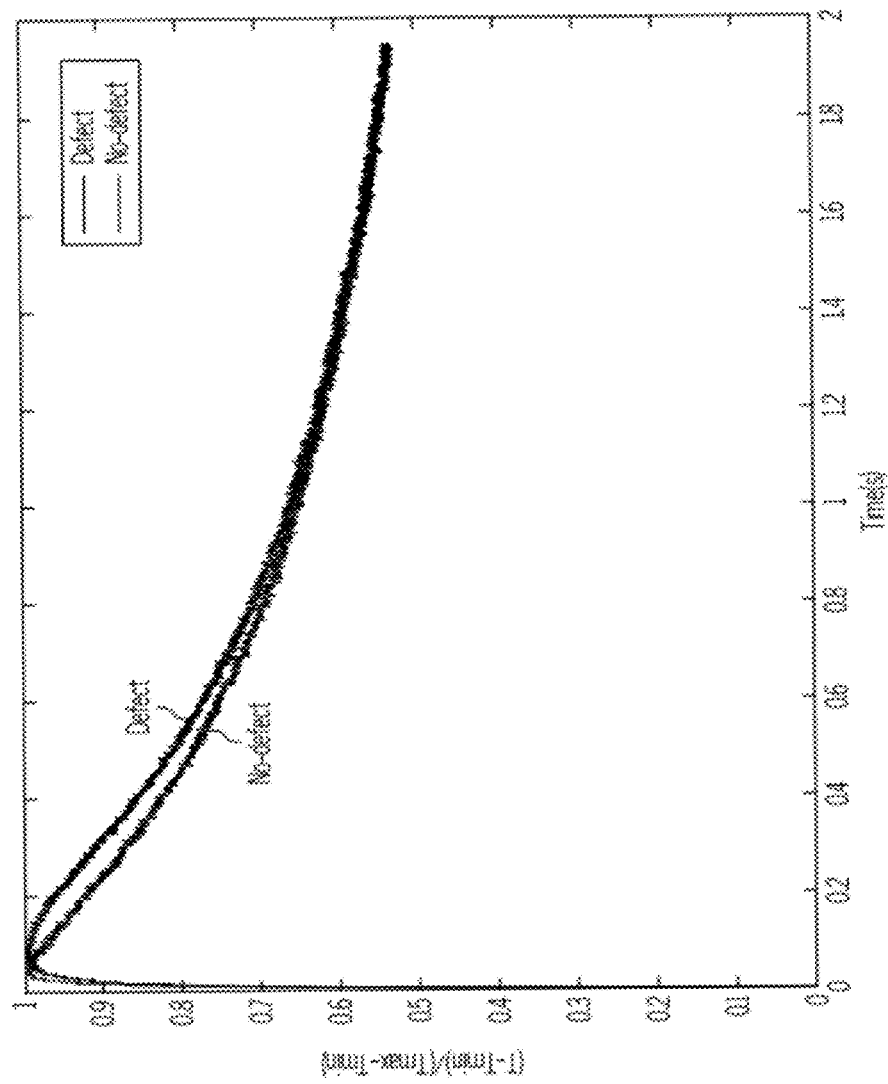
FIG. 5 depicts the temperature histories of a red colored coating with and a red colored coating without a defect.

Referring now to FIG. 5, the thermal history of a red colored coating both with and without a defect is shown over time. The data shown in FIG. 5 was collected with the apparatus depicted in FIG. 2. As illustrated in FIG. 5, the red colored coating both with and without a defect initially responds similarly to heating, i.e., the temperature initially increases rapidly to a maximum temperature. However, after being heated, the red colored coating without a defect initially cools more rapidly than the red colored coating with a defect. It is believed that the difference in the rate of cooling is due primarily to the different thermal effusivity values of the defect in the coating.

Based on the foregoing, it should be understood that different colored coatings have different thermal diffusivities and different thermal effusivities. The different values for thermal diffusivity and thermal effusivity of each color may be taken into account when determining the presence of a defect in a coating using the defect detection system 100 shown in FIG. 1 and the corresponding infrared thermographic techniques thereby improving the capability of the defect detection system to identify defects in coated substrates.

Referring again to FIG. 1, the defect detection system 100 for inspecting a coated substrate to identify defects in the coating may generally comprise a controller 104, a thermal detector 102, and at least one temperature manipulation device 106. The controller 104 may comprise a programmable logic controller (PLC) such as, for example, a computer or similar PLC operable to execute a programmed instruction set (i.e., software) or an instruction set resident on

TABLE 1

Thermal effusivities experimentally determined for different colored coatings

| Paint Color | Condition | L (m) | $t_{1/2}$ (s) | α (m²/s) | $\Delta T_{max}$ (K) | κ (W/m · K) | e (W · s^{1/2}/m²k) | Γ |
|---|---|---|---|---|---|---|---|---|
| white | No defect | $7.3 \times 10^{-4}$ | $7.3527 \times 10^{-3}$ | $10.1337 \times 10^{-6}$ | 7.466 | 36.533 | $1.1476 \times 10^4$ | N/A |
| white | defect | $8.0 \times 10^{-4}$ | $13.592 \times 10^{-3}$ | $6.58375 \times 10^{-6}$ | 7.565 | 21.375 | $0.8330 \times 10^4$ | 15.88% |
| silver | No defect | $7.0 \times 10^{-4}$ | $23.876 \times 10^{-3}$ | $2.86954 \times 10^{-6}$ | 5.654 | 14.246 | $0.8409 \times 10^4$ | N/A |
| silver | defect | $8.1 \times 10^{-4}$ | $26.591 \times 10^{-3}$ | $3.44998 \times 10^{-6}$ | 5.949 | 14.067 | $0.7571 \times 10^4$ | 5.23% |
| red | No defect | $7.0 \times 10^{-4}$ | $5.5117 \times 10^{-3}$ | $12.4304 \times 10^{-6}$ | 6.527 | 53.466 | $1.5165 \times 10^4$ | N/A |
| red | defect | $8.1 \times 10^{-4}$ | $5.6395 \times 10^{-3}$ | $16.2671 \times 10^{-6}$ | 6.136 | 60.457 | $1.4989 \times 10^4$ | 0.58% |
| green | No defect | $6.8 \times 10^{-4}$ | $5.0307 \times 10^{-3}$ | $12.8520 \times 10^{-6}$ | 6.136 | 60.522 | $1.6882 \times 10^4$ | N/A |
| green | defect | $7.8 \times 10^{-4}$ | $5.3286 \times 10^{-3}$ | $15.9643 \times 10^{-6}$ | 6.199 | 64.874 | $1.6236 \times 10^4$ | 1.95% | the hardware of the PLC (i.e., firmware). The controller 104 may comprise at least one memory storage device. Alternatively, the controller 104 may be operatively coupled to at least one memory storage device.

The thermal detector 102 may comprise any sensor or combination of sensors operable to measure thermal radiation emitted from a surface and/or the change in temperature of a surface over a period of time and convert the measured thermal radiation and/or change in temperature to an electronic data signal. In the embodiments of the defect detection system 100 shown herein, the thermal detector 102 is an infrared camera such as, for example, an SC4000 infrared camera manufactured by FLIR Inc. The thermal detector 102 is positioned a distance of 500 mm from the coated substrate and has a field of view of 120 mm by 100 mm. The thermal detector 102 is generally positioned such that the focal plane of the camera is parallel to the surface of the coated substrate. The thermal detector 102 may be electrically coupled to the controller 104. The controller 104 may be operable to send control signals to the thermal detector 102 and thereby switch the thermal detector on and off. Further, the controller 104 may be operable to receive an electronic data signal from the thermal detector 102 and analyze the data signal to identify defects, as will be described in more detail herein.

The temperature manipulation device 106 may include any device operable to increase or decrease the temperature of a coated substrate and thereby create a thermal contrast between the coating on the coated substrate and a defect in the coating. Accordingly, it should be understood that the temperature manipulation device 106 may be operable to either heat or cool a coated substrate.

In the embodiment of the defect detection system 100 shown in FIG. 1, the defect detection system comprises a pair of temperature manipulation devices 106 positioned on each side of the thermal detector 102. In this embodiment, the temperature manipulation devices 106 are operable to raise the temperature of a coated substrate through the application of radiant thermal energy. Specifically, each of the temperature manipulation devices 106 comprises six 500 watt halogen bulbs which, when activated, may increase the temperature of a coated substrate 200 positioned in front of the temperature manipulation devices 106. The temperature manipulation devices 106 are generally positioned such that the light emitted from the temperature manipulation devices is substantially normal to the surface of the coated substrate. The temperature manipulation devices 106 are electrically coupled to a power controller 105 which, in turn, is electrically coupled to the controller 104 which is operable to send a control signal to the power controller 105 and thereby switch the temperature manipulation devices 106 on and off.

Still referring to FIG. 1, the defect detection system 100 may be used in conjunction with an automated or semi-automated production or assembly line in which coated substrates are moved between production stations with a conveyor, such as a conveyor belt or an overhead conveyor system. In the embodiments shown herein, the conveyor is a conveyor belt 120. In one embodiment, in order to time the activation of the temperature manipulation devices 106 and the thermal detector 102, the defect detection system 100 may additionally include a conveyor speed detector 140 and an object detector 130. The conveyor speed detector 140 may be operable to detect the speed of the conveyor belt 120 and convert the detected speed into an electronic data signal. The conveyor speed detector 140 may be electrically coupled to the controller 104 which is operable to receive the electronic data signal indicative of the speed of the conveyor belt 120 from the conveyor speed detector 140.

The object detector 130 may comprise one or more sensors for detecting the presence of a coated substrate 200 on the conveyor belt 120 and provide the controller 104 with an electronic signal indicative of the presence of the coated substrate 200. For example, the object detector 130 may comprise a proximity sensor, an electric eye or similar type of sensor. The controller 104 is operable to receive the electronic signal from the object detector 130 and, based on the speed of the conveyor belt and the relative positioning between the object detector 130 and the temperature manipulation devices 106 and thermal detector 102, determine the appropriate timing for switching on the thermal detector 102 and temperature manipulation devices 106. In one embodiment, the object detector 130 may be further operable to detect a color of the coated substrate 200, as will be described in more detail herein.

The defect detection system 100 may be used to detect defects in a coated substrate utilizing color-based thermal mismatch. However, before the defect detection system can be used to detect defects based on color-based thermal mismatch, the defect detection system 100 must be calibrated for specific colors.

Figure 6A:
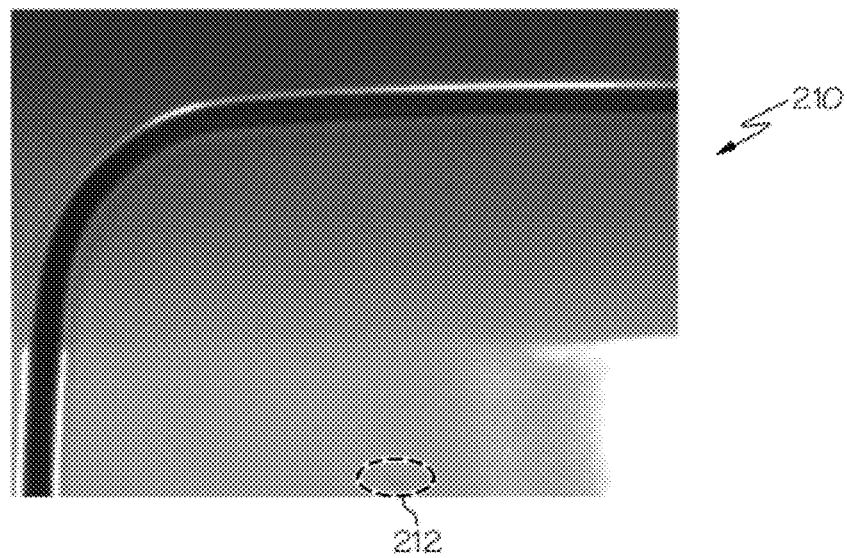
FIG. 6A depicts a thermal image of a coated substrate with a known defect which may be used to calibrate the defect detection system depicted in FIG. 1.
Figure 6B:
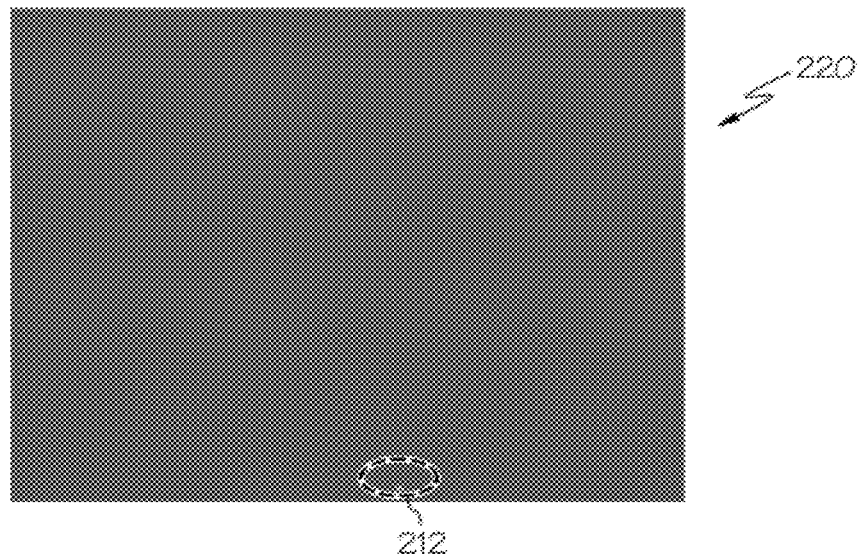
FIG. 6B depicts the thermal image of FIG. 7A after manual processing to identify the known defect and calibrate the color of the coated substrate to specific color parameters.

Referring to FIG. 1 and FIGS. 6A and 6B, the defect detection system 100 may be calibrated for specific colors by placing a coated substrate with a specified color coating and a known defect in the field of view of the thermal detector 102. The temperature of the coated substrate is then manipulated (i.e., heated in the embodiments described herein) with the temperature manipulation devices 106. In the embodiments described herein, heating may be accomplished by directing a 700 msec pulse of light onto the coated substrate 200 such that the temperature of the coated substrate is increased by about 5° C. to about 7° C.

Thereafter, a thermal image 210 of the coated substrate 200 is captured as the coated substrate cools. The thermal image is transmitted to the controller 104 where the image is stored in a memory operably associated with the controller 104 for further processing. The differences in the effusivity of the coating and the effusivity of the defect cause a thermal mismatch such that the coating and the defect have two different temperatures. However, as described above, the color of the coating also effects the thermal effusivity of the coating.

Figure 7:
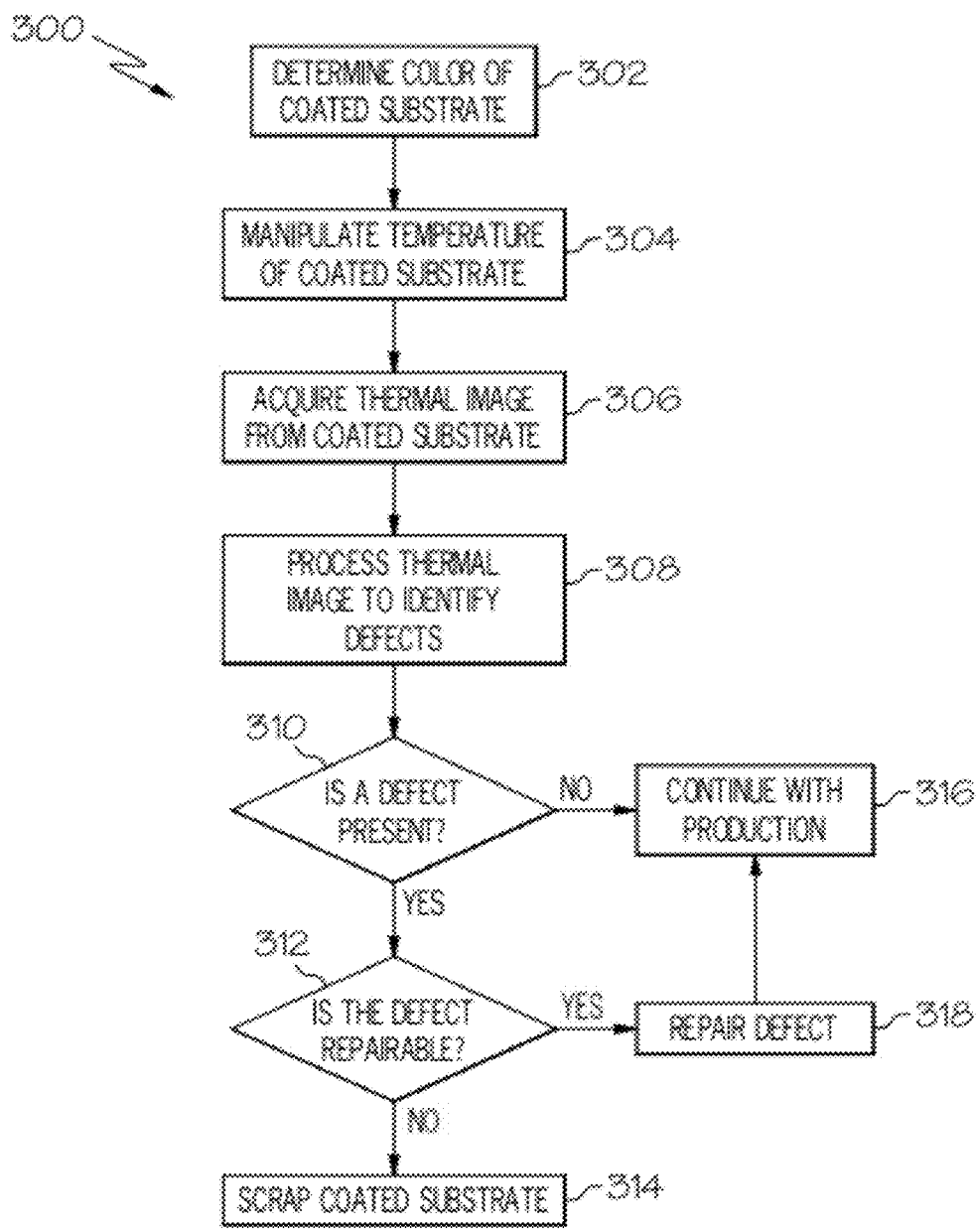
FIG. 7 is a flow diagram of one method of determining the presence of a defect in a coating utilizing color-based thermal mismatch according to one or more embodiments shown and described herein.
Figure 8:
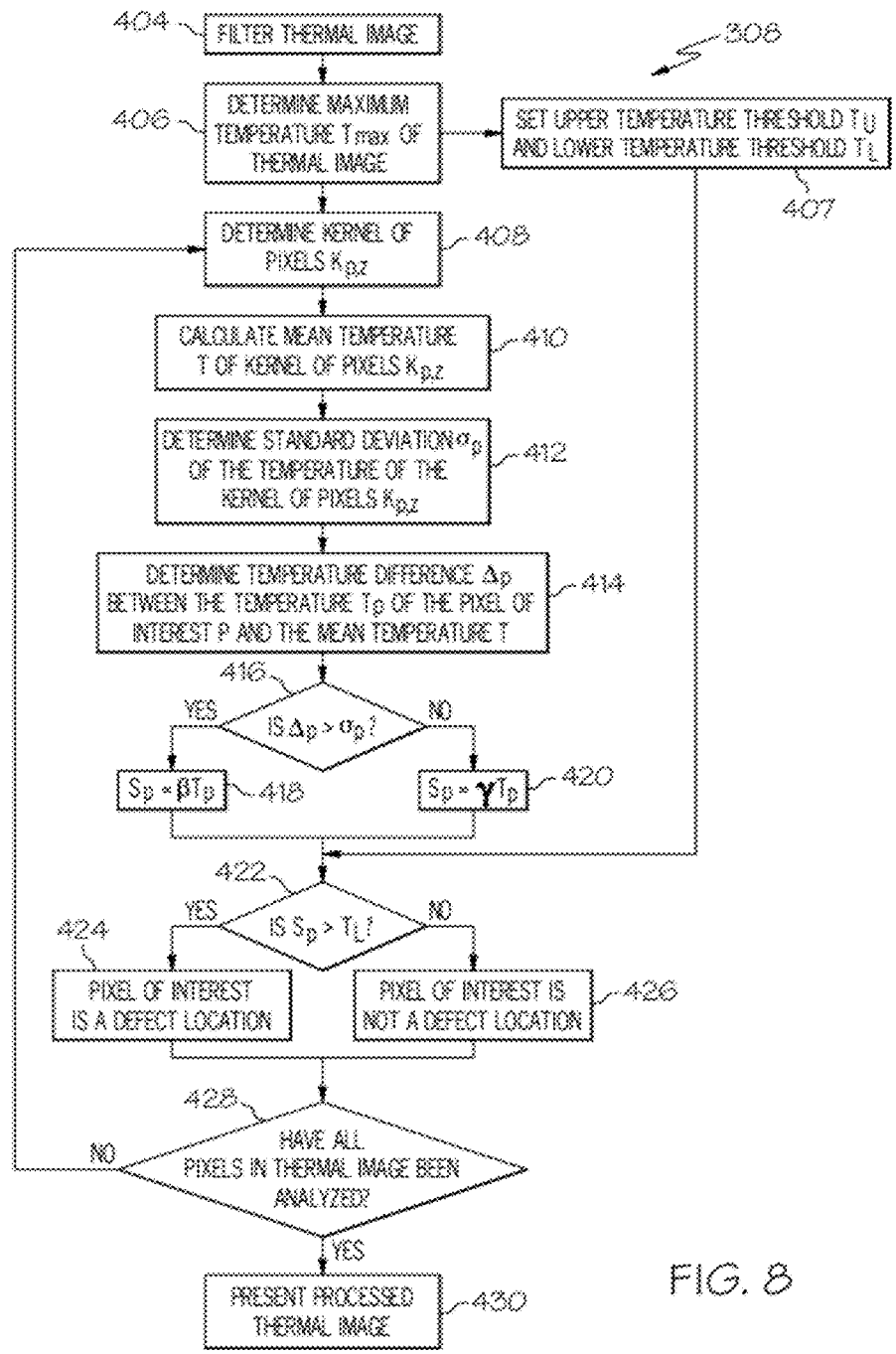
FIG. 8 is a flow diagram of one method of processing a thermal image to identify defects according to one or more embodiments shown and described herein.

In order to identify defects in the colored coating, a set of color parameters are used as will be described in more detail herein with respect to FIGS. 7 and 8. These color parameters include: the upper temperature threshold factor $\theta$; the lower temperature threshold factor $\delta$; the kernel size z; the standard deviation factor $\alpha$; the highlight factor $\beta$; and the dim factor $\gamma$. Each of the color parameters are dependent on the color of the coating applied to the substrate and thus vary with the color of the coating.

The upper temperature threshold factor $\theta$ and the lower temperature threshold factor $\delta$ are used in conjunction with the maximum temperature of the thermal image to determine an upper temperature threshold $T_U$ and a lower temperature threshold $T_L$ which bound a defect temperature range for the specific color. The upper temperature threshold $T_U = \theta T_{max}$ and the lower temperature threshold $T_L = \delta T_{max}$.

The kernel size z is an odd integer which relates to how much of an area (i.e., how many adjacent pixels) surrounding a pixel of interest P (e.g., a potential defect location) should be considered when analyzing the thermal image for a defect.

The highlight factor $\beta$ is a color parameter which is used to provide additional contrast to a pixel of interest P when the pixel of interest P is a potential defect location. The dim factor $\gamma$ is a color parameter which is used to modify the value of a pixel of interest P when the pixel of interest P is a potential defect location which has a temperature that does not vary significantly from the mean temperature of the kernel of pixels $K_{p,z}$ in which the pixel of interest P is centered.

The standard deviation factor α is a color parameter which relates to the number of standard deviations away from the mean kernel temperature the temperature $T_p$ of the pixel of interest P must be in order for the pixel of interest P to be considered a potential defect location.

In order to correlate values for the color parameters to the color of the coating, the thermal image 210 is manually processed by an operator until the known defect 212 can be located in the processed image 220 by the operator without any false positives. For example, as described above, FIG. 6A shows a thermal image 210 for a coated substrate which has a known defect 212. The thermal image 210 is manually processed by an operator using the controller 104 to adjust the color parameters for the upper temperature threshold factor θ, the lower temperature threshold factor δ, the kernel size z, the standard deviation factor α, the highlight factor β, and the dim factor γ. The color parameters are adjusted until the known defect 212 appears in the processed image without any false positives, as shown in FIG. 6B. Accordingly, it should be understood that, in at least one embodiment, the color parameters are experimentally determined. Table 2, shown below, contains examples of color parameters for several coated substrates having different colors.

TABLE 2

Color Parameters For Coated Substrates Having Different Colors

| Color | z | α | β | γ | δ | θ |
|---|---|---|---|---|---|---|
| Red | 5 | 2.65 | 0 | 15 | 0.20 | 1.0 |
| Green | 3 | 2.65 | 0 | 15 | 0.15 | 1.0 |
| White | 9 | 3.0 | 0 | 15 | 0.20 | 1.0 |
| Silver | 21 | 2.65 | 0 | 15 | 0.20 | 1.0 |

After the color parameters are experimentally determined for a color substrate having a specific color, the color parameters may be stored in a memory operably associated with the controller 104. For example, in one embodiment the color parameters are stored in a look up table (LUT) where the color parameters are indexed according to the color of the coated substrate.

Reference will now be made to FIGS. 1, 7, 8 and 9A-9B to describe a method 300 for detecting defects in a coating utilizing the defect detection system 100 in conjunction with infrared thermography incorporating color-based thermal mismatch.

As described hereinabove, the coated substrates 200 (in this example, painted automobile body panels) are positioned on a conveyor belt 120. In step 302 the color of the coated substrate 200 may be determined and input into the controller 104. In one embodiment the color of the substrate may be determined visually, such as by an operator of the defect detection system who inputs the color of the coated substrate 200 into the controller 104. In another embodiment, the color of the coated substrate 200 may be detected automatically such as with the object detector 130. For example, the object detector 130 may be an optical detector electrically coupled to the controller 104. The optical detector may be operable to detect a bar code affixed to the substrate and encoded with a part identifier as well as the color of the part. The optical detector is operable to read the bar code and send an electrical signal to the controller 104 indicative of the part identifier and the color of the coated substrate. Alternatively, the object detector may be a radio frequency (RF) receiver operable to receive an encoded RF signal indicative of the part identifier and the color of coated substrate from an RF identification tag affixed to the coated substrate. The RF receiver may be operable to pass an electrical signal to the controller indicative of the part identifier and the color of the coated substrate.

After the color of the coated substrate has been determined and relayed to the controller, the coated substrate 200 is passed in front of the defect detection system 100 on the conveyor belt 120. At step 304 the temperature of the coated substrate 200 is manipulated with temperature manipulation devices 106. In the embodiments described herein, the temperature of the coated substrate 200 is manipulated by heating the coated substrate 200 with the temperature manipulation devices 106. More specifically, based on the speed of the conveyor belt 120 (as determined by the conveyor speed detector 140) and the relative positioning of successive colored substrates (as determined by the object detector 130), the controller 104 is programmed to send a control signal to the power controller 105 which switches on the temperature manipulation devices 106 when the coated substrate is properly positioned with respect to the defect detection system 100. The temperature manipulation devices are switched on for a predetermined amount of time such that the coated substrates are exposed to a known amount of thermal energy. For example, in one embodiment, the thermal sources are switched on and off such that a 700 msec light pulse is emitted from the temperature manipulation devices 106 thereby increasing the temperature of the substrate by about 5° C. to about 7° C.

Figure 9B:
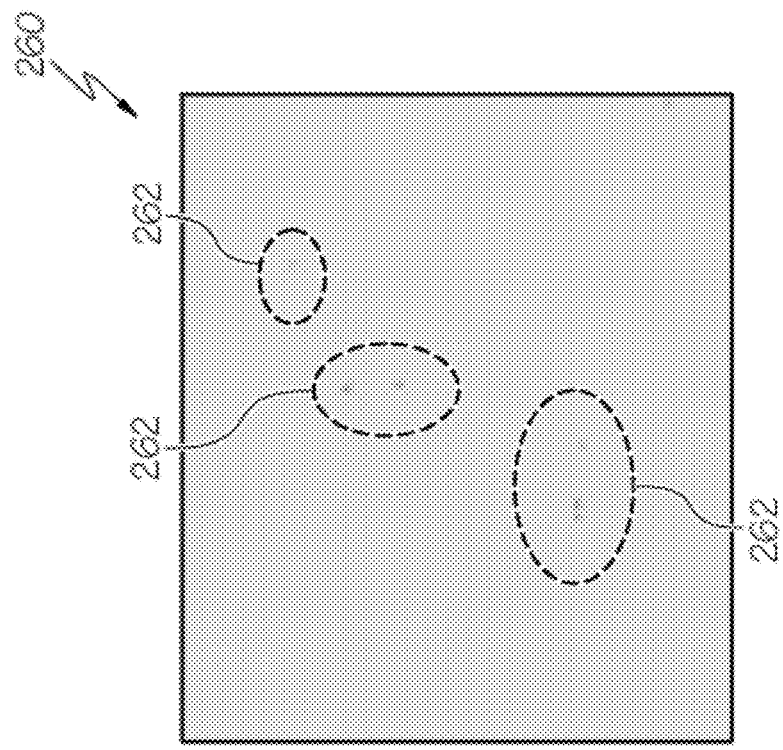
FIGS. 9A and 9B illustrate a thermal image of a coated substrate before and after processing utilizing the method of FIGS. 7 and 8.
Figure 9A:
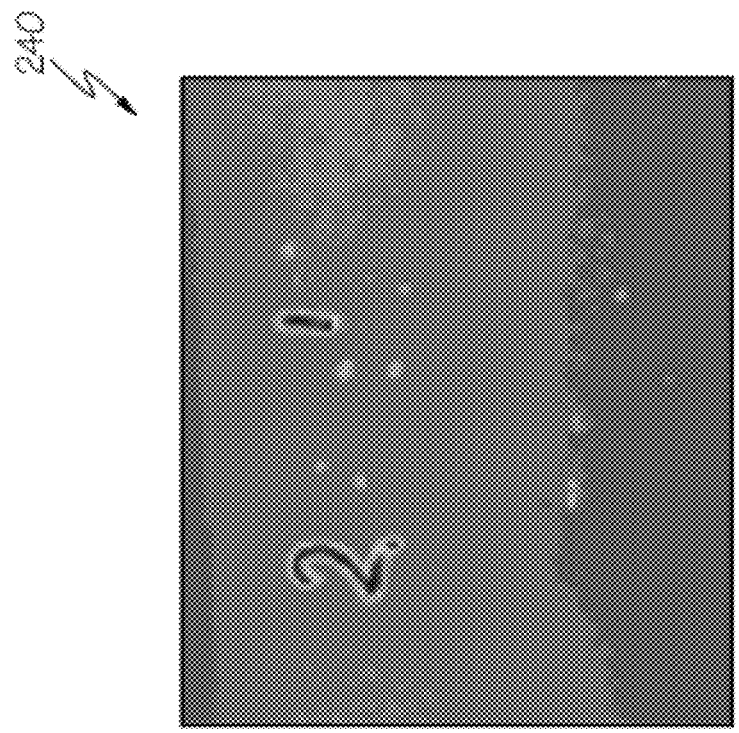
Figure 10:
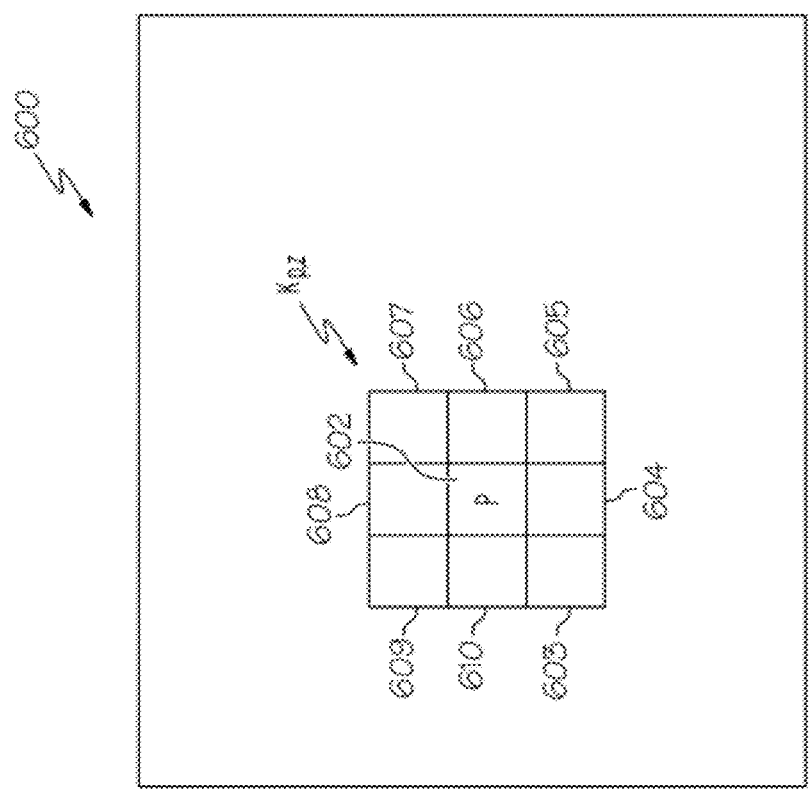
FIG. 10 schematically depicts a kernel of pixels $K_{p,z}$ according to one or more embodiments shown and described herein.

In a next step 306 a thermal image 240 of the coated substrate 200 is acquired with the thermal detector 102 after the temperature of the coated substrate 200 has been manipulated. An exemplary thermal image 240 is depicted in FIG. 9A. In one embodiment, the thermal image of the coated substrate is captured over a capture time of 100 msec following exposure to the 700 msec light pulse. The thermal image of the coated substrate consists of a plurality of discrete pixels. Each pixel has a gray scale or color value indicative of the temperature of the coated substrate at the pixel location. For example, where gray scale is used as an indicator of temperature, white may be used to indicate the upper end of the temperature scale, black is used to indicate the lower end of the temperature scale, and shades of gray are indicative of intermediate temperatures with relatively darker shades being cooler temperatures and relatively lighter shades being warmer temperatures. Where a color scale is used, red may be indicative of the upper end of the temperature scale while blue is indicative of the lower end of the temperature scale and shades of green, yellow and orange are indicative of increasingly warmer temperatures (e.g., green is cooler than yellow, yellow is cooler than orange). The temperature value of each pixel in the captured thermal image generally corresponds to the temperature of the coated substrate at the corresponding pixel location. An exemplary gray scale thermal image is shown in FIG. 10A. The acquired thermal images are then stored in a memory operatively associated with the controller 104 for further processing. In a next step 308, after the thermal image of the coated substrate 200 has been acquired, the thermal image is processed by the controller 104 to determine the presence of defects. The method of processing the thermal image to identify defects utilizing color based thermal mismatch will be described in more detail with reference to FIG. 8.

Referring now to FIGS. 1, 8 and 9A-9B, the method of processing the thermal image to identify defects in the coated substrate is schematically illustrated in a flow diagram. In an initial step 402, the controller 104 determines values for the set of color parameters based on the color of the coated substrate identified with the object detector or input into the controller by an operator. The color parameters include the upper temperature threshold factor $\theta$, the lower temperature threshold factor $\delta$, the kernel size z, the standard deviation factor $\alpha$, the highlight factor $\beta$, and the dim factor $\gamma$. As described hereinabove, each of the color parameters are dependent on the color of the coating applied to the substrate and, as such, vary with the color of the coating applied to the substrate. In the embodiments of the defect detection system 100 for detecting surface and/or subsurface defects described herein, the controller 104 is operable to determine values for the color parameters based on the color of the coating applied to the substrate. For example, in one embodiment, color parameters may be determined from a look-up table (LUT) stored in a memory operably associated with the controller and populated with values of the color parameters which are indexed according to the color of the substrate, as described above. The controller 104 may utilize the color of the coated substrate 200 to determine the proper color parameter values for the specific color applied to the coated substrate.

At step 404, the thermal image 240 is filtered to remove noise from the thermal image. In one embodiment, a Gaussian filter is utilized to remove noise from the image. However, it should be understood that other noise filtering techniques and/or noise filters may be used to filter the image at step 404.

At step 406, the controller 104 is programmed to analyze the thermal image 240 and, based on the temperature of each pixel, determine a maximum temperature $T_{max}$ of the thermal image. Thereafter, at step 407, an upper temperature threshold $T_U$ and a lower temperature threshold $T_L$ are determine based on the lower temperature threshold factor $\delta$ and the upper temperature threshold factor $\theta$. The upper temperature threshold $T_U$ and the lower temperature threshold $T_L$ define a defect temperature range for the specific color of the coating applied to the substrate. The defect temperature range may be bounded by an upper threshold temperature $T_U = \theta T_{max}$ and a lower temperature threshold $T_L = \delta T_{max}$. Both $T_U$ and $T_L$ may be determined in step 407. When the signal value $S_p$ of a pixel (as determined in steps 418 and 420) is greater than the lower temperature threshold $T_L$ and less than the upper temperature threshold $T_U$, the pixel is indicative of a defect location, as described in further detail herein. However, when the signal value $S_p$ of a pixel is less than the lower temperature threshold $T_L$, the pixel is not a defect location. When the signal value $S_p$ of a pixel (as determined in steps 418 and 420) is greater than the upper temperature threshold $T_U$, the pixel is indicative of a thermal mass, such as an agglomeration of metallic flakes embedded in the base coat and/or reflections from the edges of metallic flakes. Under these conditions, the pixel is regarded as a thermal anomaly and disregarded.

In step 408 a kernel of pixels $K_{p,z}$ for a pixel of interest P is determined based on the kernel size z. As noted hereinabove, the kernel size z may vary depending on the specific color of the coating applied to the coated substrate. In general, the kernel size z is an odd integer which relates to how much of an area (i.e., how many adjacent pixels) surrounding a pixel of interest P should be considered when analyzing the thermal image for a defect. The kernel size z generally defines a matrix of pixels having dimensions of z by z and comprising a kernel of pixels $K_{p,z}$. For example, the color green may have a kernel size of z=3 which corresponds to a region of interest comprising a 3×3 matrix of pixels where the central pixel is the pixel of interest. FIG. 11 schematically depicts a kernel of pixels $K_{p,z}$ with a kernel size of z=3 where pixel 602 is the pixel of interest P and pixels 603-610 form the kernel of pixels $K_{p,z}$. Accordingly, at step 408, the controller 104 is programmed to determine the kernel size for a pixel of interest P in the thermal image based on the color of the coating applied to the substrate.

At step 410, the mean temperature of the pixels in the kernel of pixels $K_{p,z}$ is calculated based on the temperature of each pixel in the kernel of pixels. The mean temperature $\overline{T_p}$ of the pixels may be expressed as:

$$\overline{T}_p = \sum_{i \in K_p} T_i / |K_{p,z}|.$$

At step 412 the standard deviation in the temperature of the kernel of pixels $K_{p,z}$ is calculated based on the temperature of each pixel in the kernel of pixels and the mean temperature $\overline{T_p}$ of the pixels in the kernel of pixels as determined in step 410. The standard deviation $\sigma_p$ in the temperature of the kernel of pixels may be expressed as:

$$\sigma_p = \sqrt{\sum_{i \in K_{p,z}} (T_i - \overline{T}_p)^2 / (|K_{p,z}| - 1)}.$$

At step 414 the temperature difference $\Delta_p$ between the temperature $T_p$ of the pixel of interest P (i.e., the pixel at the center of the kernel of pixels $K_{p,z}$) and the mean temperature $\overline{T_p}$ of the kernel of pixels may be determined by subtracting the mean temperature $\overline{T_p}$ from the temperature difference $\Delta_p$ such that:

$$\Delta_p = |T_p - \overline{T_p}|.$$

The value of $\Delta_p$ provides an indication of whether the temperature of the pixels surrounding the pixel of interest P varies significantly and, as such, provides an indication of whether the pixel of interest P is a potential defect location due to temperature variations which result from the differences of the thermal effusivity and thermal diffusivity at the pixel of interest P and the kernel of pixels $K_{p,z}$.

At step 416 the temperature difference $\Delta_p$ is compared to the standard deviation $\sigma_p$ of the temperature of the kernel of pixels $K_p$, as multiplied by the standard deviation factor $\alpha$. The standard deviation factor $\alpha$ is a color parameter which relates to the number of standard deviations away from the mean temperature $\overline{T_p}$ the temperature $T_p$ of the pixel of interest P must be in order for the pixel of interest P to be considered a potential defect location. As with the other color parameters, the standard deviation factor $\alpha$ varies with the color of the coating applied to the substrate.

When the temperature difference $\Delta_p$ is greater than or equal to $\alpha\sigma_p$ (i.e., when $\Delta_p \geq \alpha\sigma_p$), the pixel of interest P is a potential defect location and the method proceeds to step 418 where the signal value $S_p$ of the pixel of interest P is set. More specifically, at step 418, the signal value $S_p$ of the pixel of interest P is set to the product of the highlight factor $\beta$ and the temperature $T_p$ of the pixel of interest P (i.e., $S_p = \beta T_p$). As described above, the highlight factor $\beta$ is a color parameter which is used to provide additional contrast to a pixel of interest P when the pixel of interest P is a potential defect location. In the embodiments described herein the highlight factor $\beta$ is dependent on the color of the coating applied to the substrate.

Alternatively, when the temperature difference $\Delta_p$ is less than $\alpha\sigma_p$ (i.e., when $\Delta_p < \alpha\sigma_p$), the temperature $T_p$ of the pixel of interest P does not vary significantly from the mean temperature of the kernel of pixels $K_{p,z}$. However, the pixel of interest P may still be a potential defect location and the method proceeds to step 420 where the signal value $S_p$ of the pixel of interest P is set. More specifically, at step 420, the signal value $S_p$ of the pixel of interest P is set to the product of the dim factor $\gamma$ and the temperature $T_p$ of the pixel of interest P (i.e., $S_p = \gamma T_p$). As described above, the dim factor $\gamma$ is a color parameter which is used to modify the signal value of a pixel of interest P when the pixel of interest P is a potential defect location which has a temperature that does not vary significantly from the mean temperature of the kernel of pixels $K_{p,z}$. In the embodiments described herein the dim factor $\gamma$ is dependent on the color of the coating applied to the substrate.

After the signal value $S_p$ of the pixel of interest P has been set at either step 418 or step 420, the method proceeds to step 422 where the signal value $S_p$ is compared to the lower temperature threshold $T_L$ of the defect temperature range. If the signal value $S_p$ of the pixel of interest P is greater than or equal to the lower temperature threshold $T_L$ of the defect temperature range (i.e., $S_p \geq T_L$), the pixel of interest P is a defect location and the method proceeds to step 424. At step 424 the controller stores the location of the pixel of interest P as a defect location and set the value of the pixel of interest P to a defect value. It should be understood that all pixels identified as a defect location are set to the same defect value.

However, if the signal value $S_p$ of the pixel of interest P is determined to be less than the lower temperature threshold $T_L$ of the defect temperature range (i.e., $S_p < T_L$) at step 422, the pixel of interest P is not a defect location and the method proceeds to step 426. At step 426 the controller may store the location of the pixel of interest P as a defect location and sets the value of the pixel of interest P to a non-defect value. It should be understood that all pixels identified as non-defect locations are set to the same non-defect value and that the non-defect value is not equal to the defect value.

However, when the signal value $S_p$ of a pixel of interest P is determined to be greater than the upper temperature threshold $T_U$ of the defect temperature range (i.e., $S_p > T_U$) the pixel is indicative of a thermal mass, such as an agglomeration of metallic flakes embedded in the base coat and/or reflections from the edges of metallic flakes. Under these conditions, the pixel is regarded as a thermal anomaly at step 422 and the method proceeds to step 426. At step 426 the controller may store the location of the pixel of interest P as a defect location and sets the value of the pixel of interest P to a non-defect value. It should be understood that all pixels identified as non-defect locations are set to the same non-defect value and that the non-defect value is not equal to the defect value.

After the value of the pixel of interest P has been set to a defect value at step 424, or after the pixel of interest P has been set to a non-defect value at step 426, the method proceeds to step 428. At step 428 the controller determines if all the pixels in the thermal image have been analyzed. If all the pixels have not been analyzed, the method returns to step 408 and the method is repeated for another pixel in the thermal image. Accordingly, it should be understood that steps 408-426 of the method may be repeated for each pixel in the thermal image captured with the defect detection system 100 for detecting defects.

After all the pixels in the thermal image have been analyzed, the method proceeds to step 430. At step 430 a processed thermal image is presented. An exemplary processed thermal image is depicted at FIG. 9B. Each pixel in the processed thermal image has either a defect value or a non-defect value and, as such, the location of defects on the coated substrate can be determined. In one embodiment, the processed thermal image may be filtered to remove defects that are below a particular defect size threshold. For example, the size of a defect may be determined by calculating an area of the processed thermal image which is covered by a plurality of adjacently connected pixels having the defect value. This area may be compared to the defect size threshold and, if the area is smaller than the defect size threshold, the value of the pixels in the area may be reset to the non-defect value.

Referring again to FIGS. 1 and 7, after the thermal image has been processed to identify defects at step 308, the controller 104 may be programmed to determines if a defect is present in the coated substrate at step 310 based on the processed thermal image. If no defect is present, the controller 104 passes the coated substrate to the next step in the manufacturing process at step 316.

If at step 310 the controller 104 determines that a defect is present in the coated substrate 200 based on the processed thermal image, the method proceeds to step 312 where the controller 104 determines if the defect is repairable. In one embodiment, the controller 104 may determine if a defect is repairable based on the size of the defect, the temperature of the defect and/or combinations thereof. Alternatively or additionally, the controller 104 may be pre-programmed with empirically determined defect tolerances. The controller may compare various defect parameters (i.e., the size of the defect, the shape of the defect, the temperature of the defect) determined from the processed thermal image to the pre-programmed defect tolerances. If the defect parameters exceed the determined defect tolerances, the controller 104 determines that the defect is not repairable and the coated substrate is scrapped at step 314. However, if the defect parameters are determined to be within the pre-programmed defect tolerances, a technician may repair the defect on the spot, the coated substrate 200 may be directed to a repair queue for further handling, or the coated substrate may be flagged by the controller for repair during a subsequent manufacturing step. After the defect is repaired, the coated substrate 200 is returned to production at step 316.

The methods for determining the presence of defects utilizing color-based thermal mismatch have been described herein as being used in conjunction with a system for identifying defects. However, it should also be understood that the methods may be utilized apart from the system for detecting thermal defects. For example, the defect detection system may be used to capture a thermal image of the coated substrate while analysis of the thermal image may be performed with a separate system such as, for example, a separate computer system.

It should now be understood that the methods and systems described herein may be used to detect defects in coated substrates including, without limitation, paint coatings applied to metal, plastic or composite automobile components. Further, the systems and methods described herein may be used in conjunction with automated or semi-automated production lines as a quality control measure to reduce or mitigate the occurrence of defects in coatings applied to a substrate.

The systems and methods described herein may be used to determine the presence of defects in a coated substrate based on the color of the coated substrate. Utilizing the color of the coating applied to the substrate in conjunction with the principles of thermal mismatch improves the defect resolution capabilities of the systems and methods which, in turn, reduces the occurrence of false positives and improves the accuracy of defect detection.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. Accordingly, it is therefore intended that the appended claims cover all such changes and modifications that are within the scope of the claimed subject matter.

What is claimed is:

1. A method of analyzing a thermal image of a coated substrate to determine the presence of defects, the method comprising:
   determining a color of the coated substrate;
   determining a maximum temperature range of a coated substrate from a thermal image;
   determining a defect temperature range of the coated substrate based on the color and the maximum temperature;
   identifying a pixel of interest; and
   processing the thermal image by:
      a) determining a signal value of the pixel of interest based on:
         a temperature of the pixel of interest;
         temperatures of pixels in a kernel of pixels surrounding the pixel of interest; and
         the color of the coated substrate; and
      b) comparing the signal value to a lower temperature threshold and an upper temperature threshold of the defect temperature range, wherein the pixel of interest is a defect location when the signal value of the pixel of interest is greater than or equal to the lower temperature threshold and less than the upper temperature threshold.

2. The method of claim 1 wherein processing the thermal image further comprises:
   c) setting the signal value of the pixel of interest to a defect value when the pixel of interest is a defect; and
   d) setting the signal value of the pixel of interest to a non-defect value when the pixel of interest is not a defect.

3. The method of claim 2 further comprising repeating steps a), b), c), and d) for each pixel in the thermal image.

4. The method of claim 3 further comprising presenting a processed thermal image comprising pixels having defect values and pixels having non-defect values.

5. A method for detecting defects in a coated substrate comprising:
   determining a color of the coated substrate;
   manipulating a temperature of the coated substrate;
   acquiring a thermal image of the coated substrate;
   determining a maximum temperature of the coated substrate from the thermal image;
   determining a defect temperature range based on the color of the coated substrate and the maximum temperature of the coated substrate; and
   processing the thermal image by:
      a) determining a signal value of a pixel of interest based on:
         a temperature of the pixel of interest;
         temperatures of pixels in a kernel of pixels surrounding the pixel of interest; and
         the color of the coated substrate; and
      b) comparing the signal value of the pixel of interest to a lower temperature threshold and an upper temperature threshold of the defect temperature range, wherein the pixel of interest is a defect location when the signal value of the pixel of interest is greater than or equal to the lower temperature threshold and less than the upper temperature threshold.

6. The method of claim 5 wherein the signal value of the pixel of interest is determined by:
   determining a mean temperature of the kernel of pixels;
   determining a standard deviation of the temperature of the kernel of pixels from the mean temperature;
   determining a temperature difference between the temperature of the pixel of interest and the mean temperature; and
   comparing the temperature difference to a product of the standard deviation and a standard deviation factor, wherein:
      when the temperature difference is greater than or equal to the product of the standard deviation and the standard deviation factor, the signal value of the pixel of interest is equal to the product of the temperature of the pixel of interest and a highlight factor;
      when the temperature difference is less than the product of the standard deviation and the standard deviation factor, the signal value of the pixel of interest is equal to the product of the temperature of the pixel of interest and a dim factor; and
      the standard deviation factor, the highlight factor and the dim factor are dependent on the color of the coated substrate.

7. The method of claim 5 wherein a size of the kernel of pixels surrounding the pixel of interest is dependent on the color of the coated substrate.

8. The method of claim 5 wherein processing the thermal image further comprises:
   c) setting the signal value of the pixel of interest to a defect value when the pixel of interest is a defect; and
   d) setting the signal value of the pixel of interest to a non-defect value when the pixel of interest is not a defect.

9. The method of claim 5 further comprising repeating steps a), b), c), and d) for each pixel in the thermal image.

10. The method of claim 9 further comprising presenting a processed thermal image comprising pixels having defect values and pixels having non-defect values.

11. The method of claim 10 further comprising filtering the processed thermal image to remove defects having a size below a defect size threshold.

12. A defect detection system for detecting a defect in a coated substrate comprising a thermal detector electrically coupled to a controller and at least one temperature manipulation device coupled to the controller, wherein the controller is programmed to:
   receive an input indicative of a color of the coated substrate;
   manipulate a temperature of the coated substrate with the temperature manipulation device;
   acquire a thermal image of the coated substrate with the thermal detector;
   determine a maximum temperature of the coated substrate from the thermal image;
   determine a defect temperature range based on the color of the coated substrate and the maximum temperature of the coated substrate;
   identify a pixel of interest; and process the thermal image by:
a) determining a signal value of the pixel of interest based on:
a temperature of the pixel of interest;
temperatures of pixels in a kernel of pixels surrounding the pixel of interest; and
the color of the coated substrate; and
b) comparing the signal value of the pixel of interest to a lower temperature threshold and an upper temperature threshold of the defect temperature range, wherein the pixel of interest is a defect location when the signal value of the pixel of interest is greater than or equal to the lower temperature threshold and less than the upper temperature threshold.

13. The defect detection system of claim 12 wherein the defect detection system further comprises an object detector electrically coupled to the controller.

14. The defect detection system of claim 13 wherein the object detector is operable to output a signal to the controller indicative of the color of the coated substrate.

15. The defect detection system of claim 12 wherein the controller is further programmed determine the signal value of the pixel of interest by:
determining a mean temperature of the kernel of pixels;
determining a standard deviation of the temperature of the kernel of pixels from the mean temperature;
determining a temperature difference between the temperature of the pixel of interest and the mean temperature; and
comparing the temperature difference to a product of the standard deviation and a standard deviation factor, wherein:
when the temperature difference is greater than or equal to the product of the standard deviation and the standard deviation factor, the signal value of the pixel of interest is equal to the product of the temperature of the pixel of interest and a highlight factor;
when the temperature difference is less than the product of the standard deviation and the standard deviation factor, the signal value of the pixel of interest is equal to the product of the temperature of the pixel of interest and a dim factor; and
the standard deviation factor, the highlight factor and the dim factor are dependent on the color of the coated substrate.

16. The defect detection system of claim 12 wherein the controller is further programmed to determine a size of the kernel of pixels surrounding the pixel of interest based on the color of the coated substrate.

17. The defect detection system of claim 12 wherein the controller is further programmed to process the thermal image by:
c) setting the signal value of the pixel of interest to a defect value when the pixel of interest is a defect; and
d) setting the signal value of the pixel of interest to a non-defect value when the pixel of interest is not a defect.

18. The defect detection system of claim 17 wherein the controller is further programmed to repeat steps a), b), c), and d) for each pixel in the thermal image.

19. The defect detection system of claim 18 wherein the controller is further programmed to output a processed thermal image comprising pixels having defect values and pixels having non-defect values.

20. The defect detection system of claim 19 wherein the controller is further programmed to filter the processed thermal image to remove defects having a size below a defect size threshold.

* * * * *